(12) United States Patent
Burdio Pinilla et al.

(10) Patent No.: US 8,303,584 B2
(45) Date of Patent: Nov. 6, 2012

(54) ELECTROSURGICAL INSTRUMENT FOR TISSUE COAGULATION AND CUT

(75) Inventors: Fernando Burdio Pinilla, Castelldefels (ES); Antonio Güemes Sánchez, Zaragoza (ES)

(73) Assignees: Universidad de Zaragoza, Zaragoza (ES); Universidad de Barcelona, Barcelona (ES)

( * ) Notice: Subject to any disclaimer, the term of this patent is extended or adjusted under 35 U.S.C. 154(b) by 316 days.

(21) Appl. No.: 12/598,091

(22) PCT Filed: Apr. 30, 2008

(86) PCT No.: PCT/ES2008/000301
§ 371 (c)(1),
(2), (4) Date: Dec. 15, 2009

(87) PCT Pub. No.: WO2008/135613
PCT Pub. Date: Nov. 13, 2008

(65) Prior Publication Data
US 2010/0137856 A1    Jun. 3, 2010

(30) Foreign Application Priority Data
May 2, 2007  (ES) .................................. 200701227

(51) Int. Cl.
*A61B 18/14* (2006.01)
(52) U.S. Cl. ....................................................... 606/49
(58) Field of Classification Search ...................... 606/49
See application file for complete search history.

(56) References Cited

U.S. PATENT DOCUMENTS

| 5,707,402 A | 1/1998 | Heim |
| 6,063,083 A | 5/2000 | Duong-Van |
| 6,206,876 B1 * | 3/2001 | Levine et al. ................... 606/45 |
| 2006/0111709 A1 | 5/2006 | Goble et al. |

FOREIGN PATENT DOCUMENTS

| CN | 1295823 | 5/2001 |
| EP | 0480639 | * 4/1992 |
| WO | 01/60273 | 8/2001 |
| WO | 03/024349 | 3/2003 |

OTHER PUBLICATIONS

International Search Report issued Oct. 1, 2008 in International (PCT) Application No. PCT/ES2008/000301. Y. Sakamoto et al., "Bloodless Liver Resection Using the Monopolar Floating Ball plus Ligasure Diathermy : Preliminary Results of 16 Liver Resections", *World Journal Surgery*, 2004, vol. 28, pp. 166-172.

(Continued)

*Primary Examiner* — Lee S Cohen
(74) *Attorney, Agent, or Firm* — Wenderoth, Lind & Ponack, L.L.P.

(57) ABSTRACT

A monopolar electrosurgical instrument includes a hollow cylindrical metallic electrode which is connected to one pole of a radio frequency generator via a first end of the electrode, and a handle connected to and partially covering the electrode. The electrode includes at least one lumen to permit liquid supply of cooling liquid to the hollow electrode, a part covered with an insulative material, and a coagulating and cutting uninsulated tip. The tip includes a round ending part, a part attached to the cutting metal blade near the round ending part, and a part non-attached to the cutting metal blade. It is useful for precisely cutting the tissue that it is previously coagulated, using a single instrument, and avoiding risk of bleeding.

13 Claims, 6 Drawing Sheets

OTHER PUBLICATIONS

J. Weber et al., "New Technique for Liver Resection Using Heat Coagulative Necrosis"; *Annals of Surgery 2002*, vol. 236, No. 5, pp. 560-563.

J. Arita et al., "Randomized clinical trial of the effect of a saline-linked radiofrequency coagulator on blood loss during hepatic resection", *British Journal of Surgery 2005*, vol. 92, pp. 954-959.

C. Scudamore et al.,"Radiofrequency Ablation followed by Resection of Malignant Liver Tumors"; *The American Journal of Surgery 1999*, vol. 177, pp. 411-417.

S. Topp et al., "Saline-Linked Surface Radiofrequency Ablation. Factors Affecting Steam Popping and Depth of Injury in the Pig Liver", *Annals of Surgery*, Apr. 2004, vol. 239, No. 4, pp. 518-527.

* cited by examiner ized, the flow is between 50 and 200 ml/min.

ELECTROSURGICAL INSTRUMENT FOR TISSUE COAGULATION AND CUT

The present invention relates to the field of devices for use on surgery upon tissues. More particularly, the invention relates to electrosurgical devices that combine coagulating and cutting capabilities.

BACKGROUND ART

Liver resections are used frequently for both primary and secondary hepatic tumors and offer approximately 20% to 50% 5-year survival depending on the type of malignancy. In hepatic surgery, both blood loss and transection time are the main determinants of operative outcome. Intraoperative blood loss during liver transection has been specifically associated with preoperative complications and, in turn, perioperative blood transfusion has been reported to increase recurrence rate and decrease survival after resection of the malignancies of the liver. Therefore, in addition to the conventional clamp crushing or finger fracture techniques, other techniques such as ultrasonic dissector, water jet dissector or argon beam coagulator have been intensively employed in order to reduce intraoperative blood loss.

Electrosurgical devices generally fall into two categories, monopolar and bipolar. In a monopolar device, a radio frequency signal is supplied to an active electrode which is used to treat tissue at a target site, an electrical circuit being completed by a grounding pad which is generally a large area pad attached to the patient at a location remote from the target site. In contrast, in a bipolar arrangement, both an active and a return electrode are present on the instrument, and the current flows from the active electrode to the return electrode.

Typically, electrosurgical devices are handheld and insulated (except at the working tip) where high frequency electrical energy is delivered through a conductive element to the surgical site. If cutting of tissue is desired, a tip with a sharp or electrically focusing edge is needed. If coagulation of tissue is desired, then a blunt or electrically spreading electrode is needed. In addition, the tissue to be cauterized is often obscured by a pool of blood or smoke.

Efficient and safe liver parenchymal transection is dependent on the ability to address parenchymal division and hemostasis simultaneously. Because no single instrument adequately addresses both tasks at the same time, most hepatic parenchymal transections are performed using a combination of instruments and techniques.

One of the most recent and most efficient methods of liver transection (in terms of reduced blood loss and short transection time) involves saline-linked radio frequency technology, used either alone or in combination with other methods of division or dissection of the liver (cf. EP 1435867-A and Y. Sakamoto et al., "Bloodless liver resection using monopolar Floating Ball plus liga Sure diatehrmy: preliminary results of 16 liver resections", *Worl J Surg* 2004, vol. 28, pp. 166-172). This technology transfers radio frequency energy to the liver through saline dripping at the tip of the device. Positive features of this technology are a reduced blood loss during transection (it can be reduced to less than 200 ml of blood for a wedge resection or a segmentectomy), and a fast transection time. However, this technology still presents several drawbacks, such as the following: (1) As the technology is dependent on the rate of saline solution release, an insufficient release can cause scalding of the liver parenchyma which would make it difficult to identify blood vessels or the main hepatic ducts and, therefore, increase the chance of hilar injury during liver transection; on the other hand, an excessively saline solution release can cause an insufficient coagulation. (2) In order to achieve appropriate pre-coagulation, the devices based on this technology (even the latest models) are not sharp enough, a feature that impair and delay final cutting of the liver. (3) A depth of 3 to 5 mm of necrotic tissue is produced along the transection plane, which in cirrhotic patients with limited remnant reserve may give rise to an uncertain resection.

The approach based on the concept of pre-coagulating tissue prior to transection of the liver in order to obtain better hemostasis has been used by Weber et al. (cf. "New technique for liver resection using heat coagulative necrosis", *Ann Surg* 2002, vol. 236, pp. 560-563), who pioneered the use of radio frequency needle electrodes to obtain a 1 or 2-cm wide line of coagulation at the resection line before dividing the line with a scalpel, thereby permitting bloodless liver resection. However, this technique shows some limitations, namely, it is time-consuming, and the surgeon just coagulate the tissue with a first instrument, a second instrument being necessary to be applied in order to cut the previously coagulated tissue. In this regard, sometimes it is difficult to predict which amount of tissue is actually pre-coagulated and can be cut afterwards.

Thus, it would be useful to provide new instruments for parenchymal transections that avoid some of the limitations previously mentioned.

SUMMARY OF THE INVENTION

Inventors provide a single instrument for parenchymal transection that combine cutting and coagulating capabilities. In particular, they provide an electrosurgical instrument combining a cooled tip radio frequency electrode and a sharp blade which is attached to the electrode, specifically designed for tissue thermo-coagulation and division of the precoagulated parenchyma, which involves a substantial improvement in the radio frequency assisted resection. The electrosurgical instrument of the invention allows to precisely cut the tissue that it is previously coagulated with the same instrument, in order to avoid any risk of bleeding.

Thus, an aspect of the present invention is the provision of a monopolar electrosurgical instrument 1 for tissue coagulation and cut, comprising: a cylindrical metallic electrode which is connected to one pole of a radio frequency generator 14 on one extreme; said electrode comprising a liquid supply for cooling; a handle 7 that covers part of the electrode, a part 6 covered with an insulative material, and a coagulating and cutting uninsulated tip; said tip comprising a round ending part 2, a part 3 attached to a cutting metal blade 5 near the end, and a part 4 non-attached to the cutting metal blade.

In a particular embodiment the tissue is a parenchyma, i.e. the animal tissue that constitutes the essential part of an organ, used in anatomical nomenclature as a general term to designate the functional elements of an organ, as distinguished from its framework or stroma. Preferably, the parenchyma is liver, lung, spleen or kidney. It can also be used in uterine tissue.

In a preferred embodiment, the electrode has a diameter between 3 mm and 1 cm. In another more preferred embodiment, the diameter of the electrode is comprised between 3 mm and 6 mm. In another preferred embodiment, the liquid supply of the electrode comprises two internal lumens, one of the lumens 9 delivers a cooling solution (represented by S in the Figures) to the tip by means of a pump, such as a peristaltic pump, and the other lumen 10 returns the warmed solution to an outer collection assembly. Preferably, the cooling solution S is delivered at a rate of approximately 130 ml/min. Generally, saline solution (i.e. an aqueous physiologic solution of sodium chloride) is used as cooling solution.

Another aspect of the present invention is the provision of a radio frequency-assisted device for tissue coagulation and cut, comprising: (a) an electrosurgical instrument 1 of the type here described; (b) a source 12 of cooling solution connected to the inner part of the electrode so the cooling solution circulate until near the end of the electrode tip, by means of a pump 13; (c) an outer collection assembly 16 for collecting the used cooling solution; and (d) a radio frequency generator 14 with one pole connected to the electrosurgical instrument and the other pole connected to the body of the animal or the human, e.g. through a grounding pad 15.

Although other types of energy sources can also be used, unmodulated radio frequency current having a constant voltage and a power of 50-200 W is preferred. In particular, radio frequency in a frequency band in the range between 10 kHz and 900 kHz is used. Frequencies above 900 kHz can dissipate heat in a less controllable manner, particularly because their greater capacitive effects. The radio frequency signal is supplied to the electrode, the electrical circuit being completed by a grounding pad 15, which is generally a large area pad attached to the animal or human at a location remote from the target site. During use a voltage gradient is created at the tip of the instrument, thereby inducing current flow and related heat generation in tissue. With sufficiently high levels of electrical energy, the heat generated is sufficient to cut the tissue and, advantageously, to stop the bleeding from severed blood vessels. In a preferred embodiment, radio frequency in a frequency band in the range between 400 kHz and 500 KHz is used. The device can include a control system of the flow of the current of radiofrequency The pump 13 can be any suitable pump used in surgical procedures to provide the liquid supply at the desired flow rate, for instance, a peristaltic pump.

As it is illustrated in the accompanying Examples, comparing a saline-linked instrument known in the art with the radio frequency-assisted device of the present invention in the tissue thermocoagulation and division of the liver in an in vivo pig liver model, the radio frequency-assisted device of the present invention allows to address parenchymal division and hemostasis simultaneously, with less blood loss and faster transection time than saline-linked technology. Mean blood loss during each hepatic transection is seven times smaller with the test device than with the saline-linked method. Therefore, the radio frequency-assisted device of the present invention gives a reduction of nearly fifty percent in mean transection time, and a thirty percent increase in mean transection speed, compared to the saline-linked method.

The radio frequency-assisted device shows an improved efficiency derived from the greater coagulation depth which is similar to that found with above mentioned Weber's procedure, but such efficiency is obtained by using a handier easy-to-use hand-held instrument. Hemostasis is always achieved with the radio frequency-assisted device of the present invention without the aid of any other instrument. Furthermore, even the most up-to-date saline-linked devices are not sharp enough, what may impair and delay the final cutting of the liver. In contrast the sharp metal blade of the radio frequency-assisted device of the present invention facilitates the cutting of tissue to the precise depth of the tissue which is previously coagulated.

The radio frequency-assisted device of the present invention can also be used in image-guided radio frequency tumour ablation, as a minimally invasive thermal therapy, especially for focal metastasic and primarily liver tumors, given the significant morbidity and mortality of standard surgical resection and the large number of patients that cannot tolerate such radical surgery.

The radio frequency-assisted device of the present invention can also be used by laparoscopia.

Throughout the description and claims the word "comprise" and variations of the word, are not intended to exclude other technical features, additives, components, or steps. The disclosure in the abstract of this application is incorporated herein as reference. Additional objects, advantages and features of the invention will become apparent to those skilled in the art upon examination of the description or may be learned by practice of the invention. The following examples and drawings are provided by way of illustration, and they are not intended to be limiting of the present invention.

DETAILED DESCRIPTION OF PARTICULAR EMBODIMENTS

Figure 1:
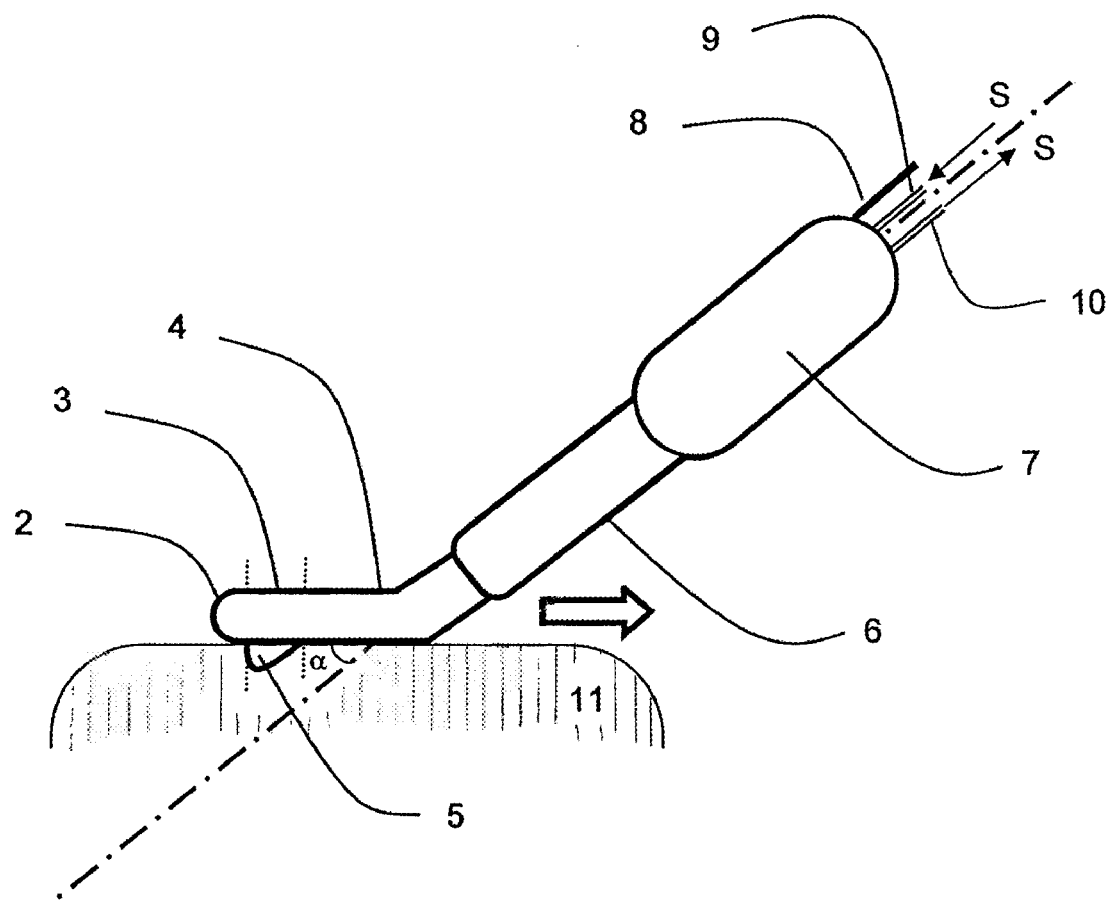
FIG. 1 is a lateral view of the electrosurgical instrument 1 showing the distal section with the metal blade, the proximal section joined to the insulated part of the electrosurgical instrument, and the advance direction of the electrosurgical instrument on the target tissue 11 (showed by the arrow direction).
Figure 5:
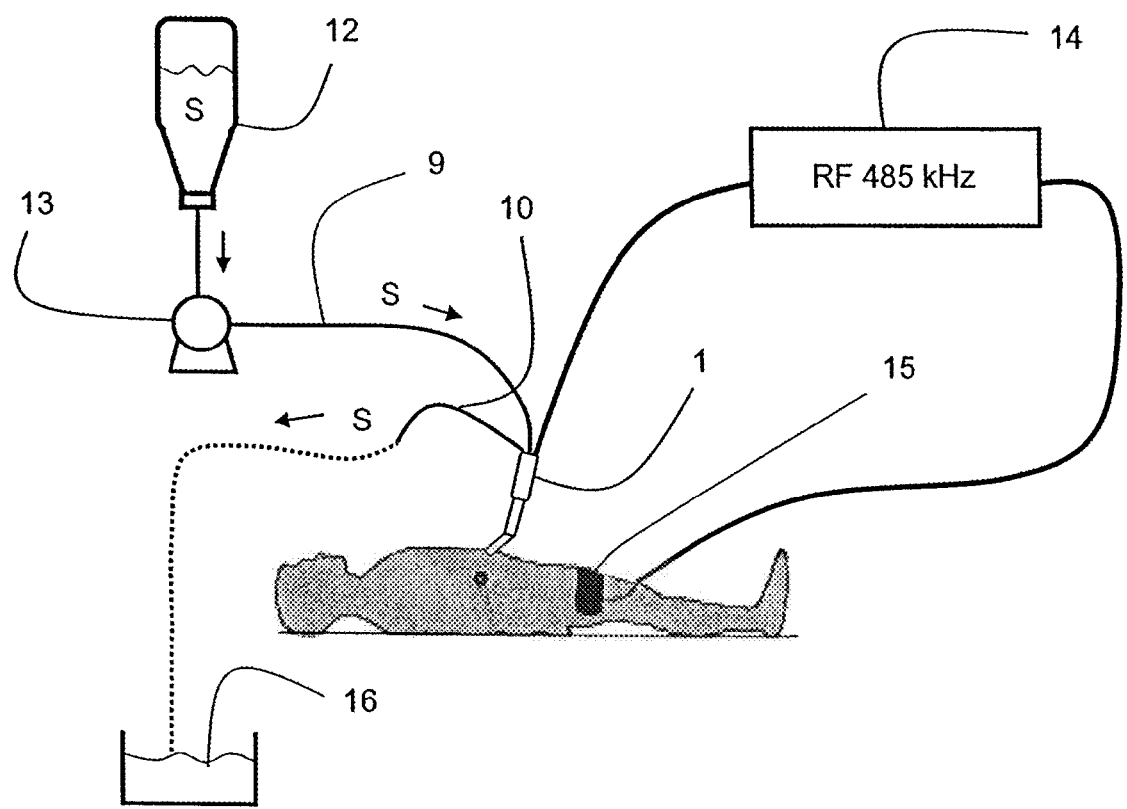
FIG. 5 is a scheme of the radio frequency-assisted device, showing an electrosurgical instrument 1, the circulation of a coiling solution S, and a radiofrequency generator.

FIG. 1 shows a scheme of a particular embodiment of the monopolar electrosurgical instrument 1 according to the present invention and FIG. 5 shows a scheme of the radio frequency-assisted device. Basically the monopolar electrosurgical instrument used is a hand-held instrument that, in a single unit, comprises the following systems: (i) a coagulating system, which is a cooled-tip electrode, having the tip electrically uninsulated, which is connected to a radio frequency generator (model CC-1; Radionics, Burlington, Mass.) at maximum power around 90 W in manual mode. This electrode comprises two internal lumens. One lumen 9 delivers chilled saline solution (0° C.) by means of a peristaltic pump (Radionics, Burlington, Mass.) at a rate of approximately 130 ml/min, to the distal tip of the electrode, and the other lumen 10 returns the warmed solution to an outer collection assembly; (ii) a cutting system which is a sharp 2 mm long metal blade 5 attached distally to the tip. The handle 7 is preferable made of sterilizable, rigid, and non-conductive material.

Figure 2A:
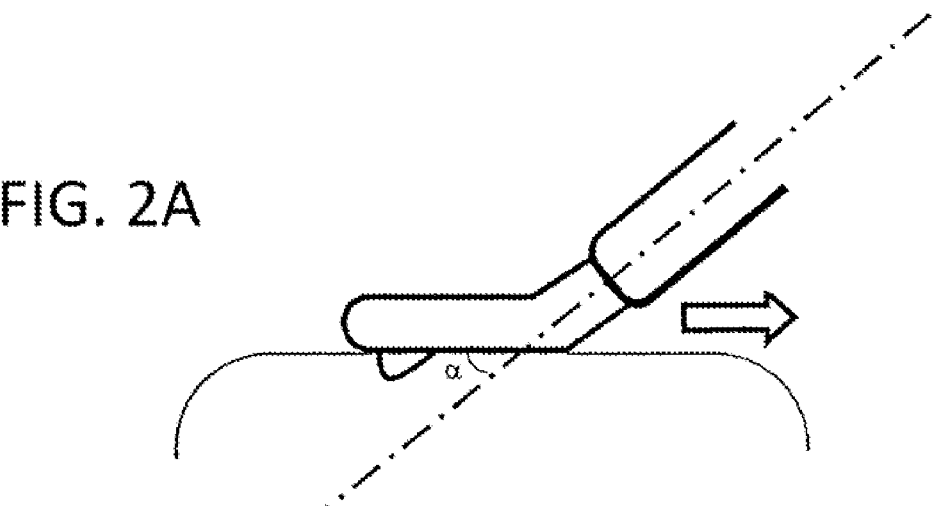
FIGS. 2A-2C are views of different variants of the tip of the electrosurgical instrument, illustrating two different curvatures FIGS. 2A and 2B and no curvature (FIG. 2C).
Figure 2B:
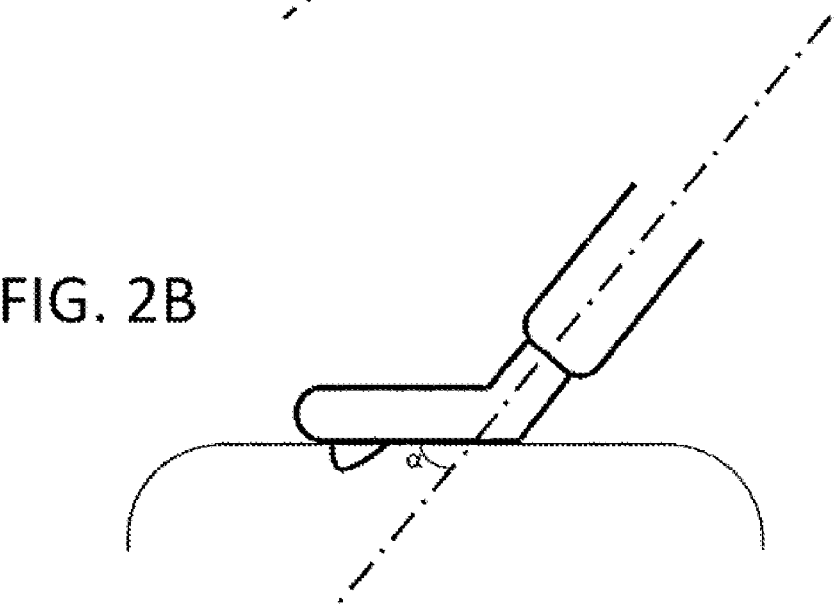
Figure 2C:
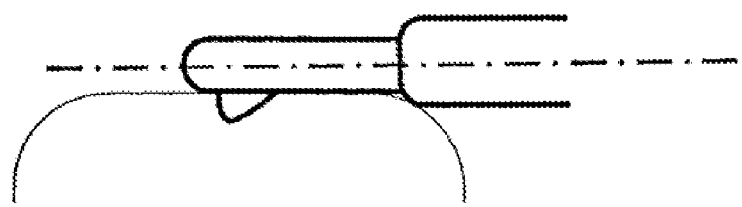
Figure 3A:
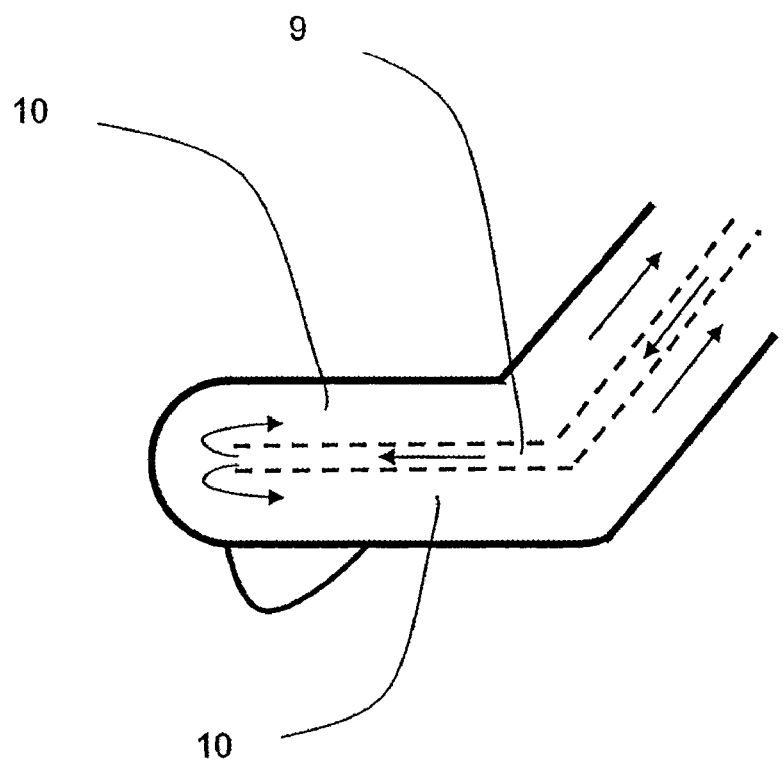
FIG. 3A is a internal view of the tip of the electrode, showing two internal lumens and the circulation of the cooling solution.
Figure 3B:
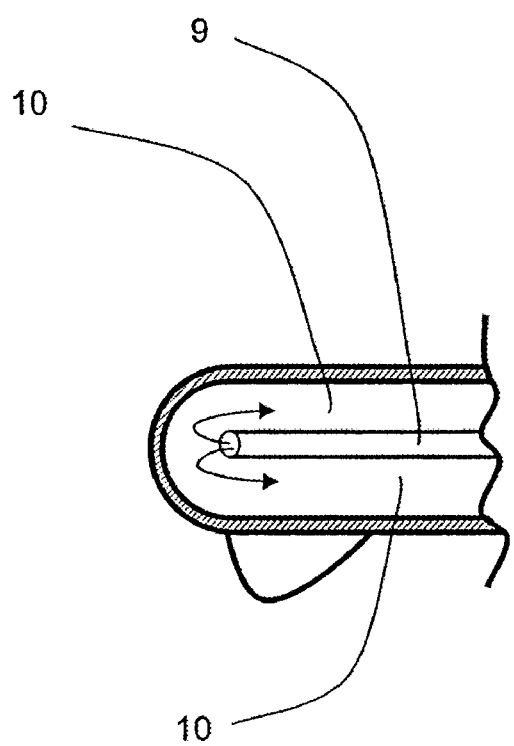
FIG. 3B is a cross-sectional view of the tip of the electrode, showing the two internal lumens.

FIGS. 2A-2C illustrate different variants of the tip of the electrosurgical instrument. In a particular embodiment, the part 4 of the tip non-attached to the cutting blade is curved. It is specially advantageuous since the tissue thermocoagulation and division of the parenchyma is a process that takes place in a confined space, and it is often difficult or inconvenient to have to re-orient the surgical instrument repeatedly in order to achieve such coagulation. Preferably, the total curvature amounts to an angle α from 40 to 60° with respect to the longitudinal axis of the electrode. More preferably the angle α is 45°.

Figure 4:
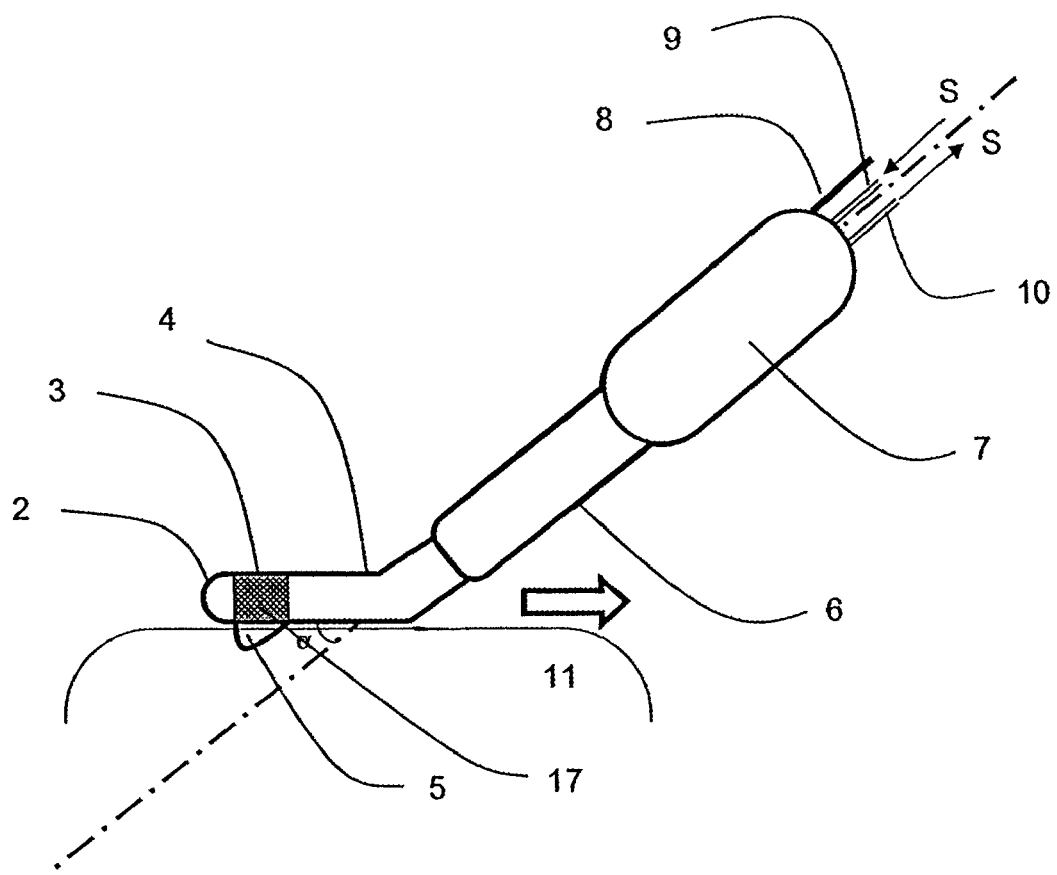
FIG. 4 is a lateral view of the electrosurgical device showing, an specific embodiment where the metallic cutting blade is insulated.

The metal blade 5 can be electrically insulated or uninsulated. In a particular embodiment, the cutting blade forms part of a metallic ring 17 and is in contact with the electrode through another ring made of electrically insulative material such as a polyamide. Thereby the cutting blade is insulated (cf. FIG. 4).

The handle 7 of the electrosurgical instrument is preferably made of sterilizable, rigid, and non-conductive material such as a polymer (e.g. polycarbonate).

The electrosurgical instrument can be used in two modes or functions that can be alternated at any time. The main function is cutting pre-coagulated tissue. The surgeon paints back the tissue to be transected with the distal non-insulated side of the instrument provided with the blade. By moving back the instrument the blunt proximal tip coagulates the tissue that is subsequently transected by the blade located distally at the tip. The cutting blade only cuts the amount of tissue that has previously been coagulated (generally 2 mm of thickness) and provides new coagulated tissue for the next painting with the instrument.

Figure 6:
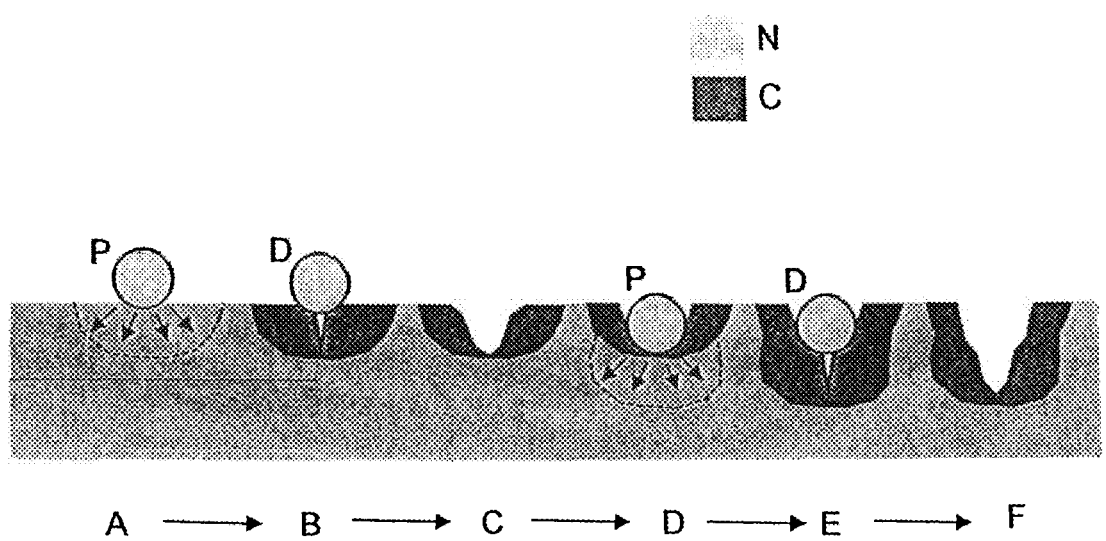
FIG. 6 is a cross view of a fragment of target tissue, showing two sequential applications of the electrosurgical instrument.

FIG. 6 illustrates the operation of the device showing the two steps carried out with the device. First the tissue is heated and coagulated by applying radio frequency currents using the proximal section (A and D). Then the cutting blade of distal section cuts the tissue previously coagulated (B and E). A, B, and C are the steps of the first application, and D, E, and F are the steps of the second application. N means non-coagulated tissue and C means coagulated tissue. The operation can be repeated as many times as needed.

Therefore, the tissue is homogeneously coagulated only once (is not overheated) due to the homogeneous cooling effect provided by the internal refrigerated closed-circuit saline infusion at the tip. The tissue does not stick to the instrument and a homogeneous depth of coagulated tissue is achieved regardless of the angle between the tissue and the instrument tip. The pre-coagulated tissue is then cut bloodlessly to a precise depth with the sharp blade attached to the tip of the instrument. In contrast to conventional saline-linked devices that provide a continuous stream of saline onto the tissue, no pooling of saline at the transection plane is observed with the radio frequency-assisted device of the present invention. Therefore, diffusion of the electric current is not impaired by an excess or scarcity of saline on the transection plane and homogenous contact is maintained with the tissue, reducing the need to use the sucker and improving visualisation of the transection plane. The secondary function of the radio frequency-assisted device of the present invention is to produce surface coagulation only. The surgeon moves the bladeless side of the instrument continuously over the tissue to be coagulated in circular passes until hemostasis is achieved.

Comparative Assay Using a Saline-Linked Instrument and the Radio Frequency-Assisted Device of the Present Invention in the Tissue Thermocoagulation and Division of the Liver in an In Vivo Pig Liver Model.

In order to test the new radio frequency-assisted device of the present invention a comparative assay with a state-of-the-art saline-linked instrument was carried out using an in vivo pig liver model. In order to evaluate the specific efficiency of division and hemostasis, each method was used without the aid of other instruments. Hemostatic stitches were employed only if the instrument was shown to be unable to control bleeding (after two minutes of intensive usage). An in vivo pig liver model was used.

Animal Model:

Female domestic farm pigs with a mean weight of 47.6 kg were used. All the experimental procedures were conducted in a laboratory authorized for animal research investigation and approved by the local Institutional Ethical Committee. Animals were deeply anesthetized with Tiletamine-Zolazepam (7 mg/kg, im), medetomidine (0.03 mg/kg) and maintained with propofol (10 mg/kg) or sevoflurane. Heart and respiration rates, saturation of peripheral oxygen ($SpO_2$), end-tidal carbon dioxide ($ETCO_2$), electrocardiogram (ECG), invasive arterial and central blood pressures were continuously monitored throughout the procedure. Four grounding pads (200-$cm^2$ each) were affixed to the back of the animal. A midline laparotomy incision was performed on every animal from xiphisternum to umbilicus to expose the liver. The inferior surface of the liver was completely isolated from the stomach and the gut by means of gauzes. A total of twenty hepatic resections were performed in the study. Four non-anatomical resections were performed on each animal. The transection plane was always perpendicular to the main axis of each lobe. In the pig, the lobes of the liver show individual surfaces and are separated by deeply extending fissures which are responsible for the great mobility. Therefore, for both practical and anatomical reasons, the level of transection was roughly at the junction of the attached and free portions of each lobe. After the experiments the animals were euthanized by exanguination.

Two groups were considered: Group A with hepatectomy performed using the radio frequency-assisted device of the present invention and Group B with Hepatectomy performed using the saline-linked dissecting sealer (DS 3.0; Tissue Link Medical, Dover, N.H.). In group B the output energy was set at around 80 W on the electrosurgical generator (Martin, Tuttlingen, Germany) and following the manufacturer's recommendations. Saline solution was dripped at a rate of approximately 4 ml/min similarly to previous references with the same device (cf. J. Arita et al., "Randomized clinical trial of the effect of a saline-linked radio frequency coagulator on blood loss during hepatic resection", *Br J Surg* 2005, vol. 92, pp. 954-959). No other instruments were used for dissection, division and hemostasis of the liver during hepatectomy. Nevertheless, if a hemorrhage was not stopped in two minutes with these devices, hemostatic stitches were used. Temporary vascular occlusion (the Pringle maneuver) was not employed.

The sample size of the study was calculated for each group by the formula proposed by R. Lehr et al. (cf. "Sixteen s squared over d squared: a relation for crude sample sizes estimates", *Stat Med* 1992, vol. 41, pp. 185-96) N=16/SMD2 where SMD is the standardised mean difference between the two means being compared. Since the method used in group A was novel, no estimate of the standard deviation of any variable was available. The first four hepatectomies were therefore employed only to estimate the standard deviation of the transection speed and thus the sample size needed according to D. G. Altman et al. (cf. "Practical statistics for medical research", London: Chapman and Hall, 1991). Taking into account this first trial and references from the literature with saline-linked methods—group B—, SMD for the transection speed was estimated as 1.44, which gave a total sample size of 16, i.e. 8 cases in each group. In the last trial a single method (group A or B) was tested in each animal.

Outcome Measures:

The comparative study was based on the measuring of different parameters. The main outcome measures were: 1) transection time: total time of transection including time for achieving complete hemostasis; 2) blood loss: total amount of blood loss during transection (from the sucker and bloody gauzes minus saline dripped onto the tissue —group B); 3) transection area: obtained by delineation of the transection plane (digital photograph) using appropriate software (3D Doctor, Able Software Corp, Lexington, Mass.); 4) transection speed: the ratio of the transection area to the transection time; and 5) blood loss per transection area.

Moreover, other secondary outcome measures were obtained: 1) risk of Biliary leakage: assessed visually over the transection surface with methylene-blue solution introduced through the main bile duct stump after removing the liver; 2) tissue coagulation depth: mean tissue coagulation depth calculated with histhological assessment from four equidistant points in the middle transverse line of the transection area; and 3) hemostatic stitches: need for hemostatic stitches after two minutes of continuous hemorrhage.

Histological Assessment:

Only selected histologic samples were submitted for microscopic review. Specimens were fixed in formalin, paraffin embedded, cut and stained with hematoxylin and eosin. Microscopic findings of coagulative necrosis (cytoplasmic shrinkage, densification and variable degree of chromatin condensation with focal formation of apoptoticlike bodies) were looked for. Viability of liver cells was assessed by staining for oxidate pathway enzymes by a modification of the Nottingham method (University of Nottingham Medical School Division of Histhopatology; http://www.nottingham.ac.uk/pathology/protocols/nadh.html) using adenine dinucleotide (NADH) as described by C. H. Scudamore et al. (cf. "Radio frequency ablation followed by resection of malignant liver tumors", *Am J Surg* 1999, vol. 177, pp. 411-417) and Topp (cf. S. A. Topp et al., "Saline-linked surface radio frequency ablation. Factors affecting steam popping and depth of injury in the pig liver", *Ann Surg* 2004, vol. 239, pp. 518-527).

Statistical Analysis:

Main and secondary outcome measures were compared and correlated among both groups. The Kolmogorov-Smirnov test was used to determine whether values followed a normal distribution. Mean values of numerical data were compared through both groups using the Student t test or the U-Mann-Whitney's test when appropriate. Categorical data were compared through both groups using Fisher's exact text. Differences in variables were considered to be significant at a threshold of $p<0.05$. Statistical analyses were performed with statistical software (version 12.0; SPSS, Chicago, Ill.).

Results:

All the pigs tolerated the procedures well with appropriate intravenous fluid administration. No relevant complications were described with any method during or after the operative procedure. During transection one or two vein vessels often with more than 5 mm in diameter were encountered usually at the center of the transection plane.

These large vessels required in almost all cases (7/8) of group B one or two stitches to achieve complete hemostasis after two minutes of continuous bleeding in spite of painting tight circles around the bleeders with the saline-linked device (following manufacturer's recommendations). Conversely, in group A complete hemostasis was always achieved with radio frequency-assisted device alone and without the need for hemostatic stitches in any case (0/8). Therefore, mean blood loss during each hepatic transection was more than seven times smaller with the test device than with the saline-linked method. These differences between groups were maintained when blood loss relative to the transection area was examined. The radio frequency-assisted device of the present invention therefore gave a reduction of nearly fifty percent in mean transection time and a thirty percent increase in mean transection speed compared to the saline-linked method. The results obtained are shown in Table 1.

TABLE 1

Evaluation of numerical variables

| | Group A (Proposed device) | Group B (Tissue-Link ®) | Probability (P)* |
|---|---|---|---|
| Transection time (min) | 11.95 ± 2.48 | 21.02 ± 6.61 | 0.006 |
| Blood loss (ml) | 69.75 ± 73.93 | 527.00 ± 273.29 | 0.001 |
| Transection area (cm$^2$) | 34.83 ± 6.54 | 41.01 ± 8.34 | N.S. |
| Transection speed (cm$^2$/min) | 2.97 ± 0.39 | 2.06 ± 0.51 | 0.002 |
| Blood loss per transection area (ml/cm$^2$) | 1.82 ± 1.56 | 12.85 ± 6.14 | 0.001 |
| Tissue coagulation depth (mm) | 5.90 ± 1.61 | 3.37 ± 1.40 | 0.005 |

*Differences in variables were considered to be significant at a threshold of $p < 0.05$.
N.S means no significant differences Both transection surfaces after each hepatectomy showed similar macroscopic features in both groups with the typical bloodless pale-gray aspect. No relevant differences between both groups were encountered microscopically either. In both groups three zones of tissue viability were observed. However, a greater mean coagulation depth ($p=0.005$) in group A compared to group B was found in the cross section plane as it is shown in Table 1. Risk of biliary leakage estimated by leakage of methylene-blue test on the transection surface was observed in two cases (2/8) in group B and in one case (1/8) in group A. This difference did not reach statistical significance.

A seven-fold reduction in mean blood loss and blood loss relative to transection surface during transection when using the test device compared to the saline-linked device group was also observed. A reduction to less than 200 ml of blood loss for a wedge resection or segmentectomy usually in a clinical setting with saline-linked technology has been reported, and Arita et al. demonstrated a blood loss per unit transection area of 7.0 ml/cm2 (cf. "Randomized clinical trial of the effect of a saline-linked radio frequency coagulator on blood loss during hepatic resection", *Br J Surg* 2005, vol. 92, pp. 954-959). The relative mean greater blood loss with saline-linked technology encountered in the present invention (527.00±273.29 ml) was attributed to: (i) hepatectomies were performed without the Pringle maneuver; and (ii) the device was employed alone for both transection and hemostasis of the liver for up to two minutes of intensive usage. Nonetheless, the extremely low mean blood loss and mean blood loss per transection area achieved with the test device in this setting showed that it is more efficient than the saline-linked device in reducing blood loss during transection.

A thirty percent increase in mean transection speed when using the test device over the saline-linked device group (2.97±0.39 and 2.06 cm$^2$/min for group A and B, respectively) was also observed. Arita et al. demonstrated a transection speed of 0.99 cm$^2$/min for saline-linked technology and 0.89 cm$^2$/min for clamp crushing technique in a clinical setting. Therefore, even though transection speed with the saline-linked technology was better in the experimental setting of the invention than that reported by Arita et al., a significantly improved transection time in the proposed device group over the saline-linked device group was demonstrated in the same setting.

With the proposed method a greater mean coagulation depth was obtained compared to the saline-linked device (5.90±1.61 mm and 3.37±1.40 mm, for groups A and B, respectively) and this was the only macroscopic or microscopic difference found in both transection surfaces between the groups.

In conclusion, the radio frequency-assisted device of the present invention has shown to address parenchymal division and hemostasis simultaneously, resulting in reduced blood loss and shorter transection time compared to saline-linked technology.

The invention claimed is:

1. A monopolar electrosurgical instrument for tissue coagulation and cut, comprising:
    a hollow cylindrical metallic electrode which is adapted to be connected to one pole of a radio frequency generator via a first end of said hollow electrode; and
    a handle connected to said hollow electrode and partially covering said hollow electrode;
    wherein said hollow electrode comprises
        at least one lumen to permit liquid supply of cooling liquid to said hollow electrode,
        a part covered with an insulative material, and
        a coagulating and cutting uninsulated tip,
        said tip comprising
            a round ending part,
            a part attached to a cutting metal blade near said round ending part, and
            a part non-attached to said cutting metal blade.

2. The instrument according to claim 1, wherein said hollow electrode has a diameter between 3 mm and 1 cm.

3. The instrument according to claim 2, wherein said hollow electrode has a diameter between 3 and 6 mm.

4. The instrument according to claim 1, wherein said at least one lumen comprises two internal lumens, one of the lumens being arranged to deliver a cooling solution via a pump to the tip of said hollow electrode, and the other lumen being arranged to return warmed solution to an outer collection assembly.

5. The instrument according to claim 4, wherein the part non-attached to the blade is curved.

6. The instrument according to claim 1, wherein the part non-attached to the blade is curved.

7. The instrument according to claim 6, wherein the part non-attached to the blade has a total curvature amounting to an angle α from 40 to 60° with respect to a longitudinal axis of said hollow cylindrical metallic electrode.

8. The instrument according to claim 7, wherein the angle is 45°.

9. The instrument according to claim 1, wherein the metal blade forms part of a metallic ring, which is in contact with the electrode through an annular piece of a non-conductor material, such that the metallic blade is electrically isolated.

10. A radio frequency-assisted device for tissue coagulation and cut, comprising:
    (a) an electrosurgical instrument as defined in claim 1;
    (b) a source of cooling solution connected to an inner part of said hollow electrode so the cooling solution circulates near the round ending part of the tip of said hollow electrode, via a pump;
    (c) an outer collection assembly connected to the inner part of said hollow electrode for collecting used cooling solution; and
    (d) a radio frequency generator having a first pole connected to the electrosurgical instrument and a second pole adapted to be connected to a body of an animal or a human.

11. A radio frequency-assisted device for tissue coagulation and cut, comprising:
    (a) an electrosurgical instrument as defined in claim 4;
    (b) a source of cooling solution connected to an inner part of said hollow electrode so the cooling solution circulates near the round ending part of the tip of said hollow electrode, via a pump;
    (c) an outer collection assembly connected to the inner part of said hollow electrode for collecting used cooling solution; and
    (d) a radio frequency generator having a first pole connected to the electrosurgical instrument and a second pole adapted to be connected to a body of an animal or a human.

12. A radio frequency-assisted device for tissue coagulation and cut, comprising:
    (a) an electrosurgical instrument as defined in claim 6;
    (b) a source of cooling solution connected to an inner part of said hollow electrode so the cooling solution circulates near the the rounding end part of the tip of said hollow electrode, via a pump;
    (c) an outer collection assembly connected to the inner part of said hollow electrode for collecting used cooling solution; and
    (d) a radio frequency generator having a first pole connected to the electrosurgical instrument and a second pole adapted to be connected to a body of an animal or a human.

13. A radio frequency-assisted device for tissue coagulation and cut, comprising:
    (a) an electrosurgical instrument as defined in claim 9;
    (b) a source of cooling solution connected to an inner part of said hollow electrode so the cooling solution circulates near the round ending part of the tip of said hollow electrode, via a pump;
    (c) an outer collection assembly connected to the inner part of said hollow electrode for collecting used cooling solution; and
    (d) a radio frequency generator having a first pole connected to the electrosurgical instrument and a second pole adapted to be connected to a body of an animal or a human.

* * * * *